US010753841B2

(12) United States Patent
Shaw et al.

(10) Patent No.: US 10,753,841 B2
(45) Date of Patent: Aug. 25, 2020

(54) DRY HEAT DIFFUSION CELL AND DIFFUSION SAMPLING SYSTEM

(71) Applicant: Teledyne Instruments, Inc., Thousand Oaks, CA (US)

(72) Inventors: Steven W. Shaw, Simi Valley, CA (US); Gary C. Downes, Moorpark, CA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 198 days.

(21) Appl. No.: 16/102,480

(22) Filed: Aug. 13, 2018

(65) Prior Publication Data

US 2019/0353570 A1 Nov. 21, 2019

Related U.S. Application Data

(60) Provisional application No. 62/673,733, filed on May 18, 2018.

(51) Int. Cl.
| | | |
|---|---|---|
| *G01N 13/00* | (2006.01) | |
| *G01N 33/15* | (2006.01) | |
| *G01N 35/10* | (2006.01) | |
| *G01N 35/00* | (2006.01) | |

(52) U.S. Cl.
CPC ............ *G01N 13/00* (2013.01); *G01N 33/15* (2013.01); *G01N 35/1004* (2013.01); *G01N 35/1081* (2013.01); *G01N 2013/003* (2013.01); *G01N 2035/00356* (2013.01); *G01N 2035/00534* (2013.01)

(58) Field of Classification Search
CPC .... G01N 13/00; G01N 33/15; G01N 35/1004; G01N 2035/00356; G01N 2013/003; G01N 2035/00534; G01N 35/1081; G01N 2013/006; G01N 1/38; G01N 2001/381; G01N 11/04; G01N 11/06; G01N 2035/0036; G01N 2035/00376
USPC .............. 422/68.1, 500, 560–562, 292, 307; 73/866, 863.01, 863.11, 863.23, 863.31, 73/864.81, 864.91, 865.5, 61.63; 366/140; 220/4.26, 4.27, 200, 254.1
See application file for complete search history.

(56) References Cited

U.S. PATENT DOCUMENTS

| | | |
|---|---|---|
| 5,198,109 A | 3/1993 | Hanson et al. |
| 5,296,139 A | 3/1994 | Hanson et al. |
| 6,821,419 B2 | 11/2004 | Hanson et al. |
| 2012/0000275 A1* | 1/2012 | Gilbert .................. G01N 33/15 73/61.43 |

(Continued)

*Primary Examiner* — Robert R Raevis
(74) *Attorney, Agent, or Firm* — Cislo & Thomas, LLP

(57) ABSTRACT

A diffusion system to improve the efficiency, accuracy, and consistency of testing the release rate of an active ingredient in semisolid form through a membrane in between a dosage lid and a cell cap mounted on a cell in which a mixer is placed to mix the receptor medium in the cell as the semisolid diffuses through the membrane. The cell can be placed in a heating system to heat the samples. The cell has a sampling arm through which samples of the receptor medium can be extracted without opening the cell cap and dosage lid. The mixer may be cylindrical and may occupy a large surface area of the cell. The mixer may have grooves and other irregularities to increase turbulence while mixing. The system can be automated using an automated sampling and collection station.

22 Claims, 15 Drawing Sheets

(56) References Cited

U.S. PATENT DOCUMENTS

2017/0072393 A1\* 3/2017 Jackson ............. B01L 3/50825
2019/0242863 A1\* 8/2019 Garbacz ................ G01N 13/00

\* cited by examiner

DRY HEAT DIFFUSION CELL AND DIFFUSION SAMPLING SYSTEM

CROSS-REFERENCE TO RELATED APPLICATION

This patent application claims the benefit of U.S. Provisional Patent Application Ser. No. 62/673,733, entitled "Dry Heat Diffusion Cell and Diffusion Sampling System," filed May 18, 2018, which application is incorporated in its entirety here by this reference.

TECHNICAL FIELD

The invention described herein generally relates to a dry heat diffusion cell testing system.

BACKGROUND

Diffusion testing is a release rate test of an active pharmaceutical ingredient in semisolid form as it permeates through a skin-like or synthetic membrane into solution. Diffusion replicates the process of skin-applied medicine as it permeates the skin into the body for local or systemic action. It is ideal for the quality control of topical preparations. Semisolid preparations such as creams, ointments, and gels must penetrate the layers of the skin to have benefit. Topical pharmaceutical formulations, designed to permeate the skin, require in vitro release-rate testing that can produce reliable and consistent results. Diffusion testing measures the rate that an active pharmaceutical ingredient is released from a semisolid preparation, providing the quality control analyst with critical performance data. Diffusion testing using diffusion cells has become the industry standard due to the pioneering work of Dr. T. J. Franz who developed the "Franz cell." This device consists of a small-volume, water-jacketed cell that contains a chamber for drug application, a membrane through which the drug may permeate, and a receptor media chamber from which samples may be extracted and analyzed for drug release. The chamber for drug application, however, often times suffers from imprecise manufacturing resulting in misalignment of components in the drug application chamber, which causes variations in results across test samples in the same batch.

A traditional diffusion testing system typically has a group of six cells for simultaneous testing of six specimens. A magnetic cell drive controls the mixing of each cell receptor chamber throughout the test, and a circulating bath provides heated water to the jacketed cells to maintain temperature. As such, traditional diffusion systems occupy a large footprint, have inefficient control of temperatures due to the water bath, create large variances in results due to imprecisions in the diffusion cells, and are difficult to automate. For the foregoing reasons there is a need for an improved diffusion system to address these issues.

SUMMARY OF THE INVENTION

The invention of the present application is a diffusion system. In a preferred embodiment, the diffusion system comprises a cell for receiving a receptor medium, a mixer configured to fit inside the cell to mix the receptor medium in the cell, a cell cap to cover the cell, and a dosage lid to place on top of the cell cap. In some embodiments, a membrane is also provided to place in between the cell cap and the dosage lid. The membrane is sometimes configured to mimic skin, for example, to test the rate of which a semi-solid compound can diffuse through the membrane into the receptor medium. In some embodiments, the diffusion testing system further comprises a heating system. In some embodiments, the diffusion testing system further comprises an automated sampling and collection station.

The cell is designed for precision, versatility, and ease-of-use in diffusion-testing labs. In the preferred embodiment, the cell comprises a main body having an open top, and a sampling arm having an opening branching from the main body. In manual sampling applications, the wide opening in the arm accommodates standard pipette tips and allows for complete mixing of the receptor solution within the cell. For maximum versatility, lab analysts can choose from small, medium, or large borosilicate glass cells and, using the volume-adjustment mixer, can obtain receptor media volumes from 10 mL to 30 mL.

The cell cap is placed on top of the cell at the open top. The cell cap has an orifice diameter to allow access into the cell through the open top. An array of cell cap kits accommodates all 25 mm membranes, and can accommodate orifice diameters from 1 mm to 20 mm, and can accommodate dosage volumes from 0.25 mL to 6.2 mL. A convenient fill mark on the sampling arm indicates when the cell is filled. Cell preparation, including dosage application, bubble detection, and bubble removal, is fast and easy. The cells are configured to be easily inserted and removed from a heating block of the heating system.

The dosage lids are configured to fit on top of the cell caps with the membrane residing therebetween. Dosage lids also have an orifice. The cell caps and dosage lids are machined to very tight tolerances so that the orifice of the cell cap aligns precisely with the orifice of the dosage lid to ensure uniform and consistent surface area exposure of the exposed membrane from one cell to the next, thereby leading to reduced test variability.

The mixers are configured to mix the receptor media in the cell. Preferably, the mixers have magnets. Preferably, mixers occupy nearly the full diameter of the cell. As the cells are generally cylindrical in shape, the mixers are also cylindrical in shape defining a longitudinal axis. Preferably, the mixers have transverse and longitudinal grooves for efficient mixing and pumping of receptor media. The longitudinal groove is formed longitudinally within the wall of the mixer. Preferably, the longitudinal groove is angled relative to the longitudinal axis. The transverse groove is formed along the top surface of the mixer. Any kind of irregularity along the top surface of the mixer can be used to create turbulence in the receptor media. For example, the top surface may have undulations, projections, crevices, fins, peaks and valleys, and the like. The bottom of the mixer may be flat. Preferably, the bottom of the mixer is rounded or convex. This configuration facilitates efficient spinning of the mixer by reducing the surface area in contact with the bottom of the cell. The height of the mixer can be variable. The selected height will depend on the amount of volume to be displaced in the cell. Therefore, the user can determine the volume of the receptor medium by selecting a mixer with a particular height.

The heating system is used to heat the cells and receptor media to desired temperatures. In the preferred embodiment, the heating system comprises a dry heat block. The dry heat block provides a compact footprint for six-cell testing, although the heat block can be configured to receive any number of cells. Precision heating and stirring systems contained within the block makes the system fully portable, able to be placed in any position the analyst chooses for faster, easier cell preparation. Precise control of mixing speeds may range from about 200 rpm to about 900 rpm, temperatures may range from about 25° C. to about 40° C., and the system may meet or exceed USP <1724> specifications. In some embodiments, an advanced color touch screen controller running on an embedded single-board computer with a built-in SQL database and real-time clock provides advanced monitoring, diagnostic, and reporting capabilities, user-friendly programming and navigation, storage for up to 100 test protocols, and configurable security for up to 50 users. A large, bright display allows key parameters to be seen from a distance, including speed, temperature, elapsed time, and time to next sample. When sampling is due, the system alerts the operator with the cell position, a countdown timer, and an audible beep. Test reports are delivered via a printer. In some embodiments, the controller may have a magnet at its base to easily attach to the dry heat block.

The dry heat block may comprise any number of bays to receive the cells. The bays are uniform in size and configured to receive the largest diameter cells. In some embodiments, to accommodate cells of smaller diameter, cell sleeves may be provided. The cell sleeve has an outer wall having an outer diameter that is substantially similar to the diameter of the bay so as to fit inside the bay. The cell sleeve also has an inner wall defining a cavity, the inner wall having an inner diameter that is smaller than the outer diameter. Different cell sleeves can have different sized inner diameters to accommodate the smaller cells. For example, if three different sized cells are provided, then two sleeves may be offered. The largest cell size can be inserted into a bay of the dry heat block without a sleeve. The medium-sized cell can be inserted into a first-sized sleeve having an inner diameter substantially the size of the diameter of the medium-sized cell to receive the medium-sized cell. The small-sized cell can be inserted into a second-sized sleeve having an inner diameter substantially the size of the small-sized cell to receive the small-sized cell. Any of the sleeves can be inserted into the bays of the dry heat block to transfer heat from the dry heat block to the sleeves, which transfer the heat to the cells. The sleeves have walls that substantially cover the cell with some openings to view the receptor media.

The dry heat block utilizes a magnet system to rotate the mixer to stir the receptor media. In the preferred embodiment, each bay has a separate motor to drive the magnets to spin the mixers. The motors can be fixed speed or variable speed. Variable speed motors can be controlled by the user, pre-programmed, or programmable.

The diffusion system refines the art of diffusion testing by incorporating breakthroughs in four areas: diffusion cell design; heating and stirring; automated sampling and collection; and computerized control. As discussed above, the dry heat diffusion cell at the heart of the system delivers significantly improved test results as compared to traditional water-jacketed, displacement-sampling systems. In addition, the precision heating and stirring components built into each of the six-cell blocks provide outstanding control of temperature and speed.

Although sampling and collection can be performed manually, to further improve the efficiency of the system, the sampling and collection can be automated. Automatic sampling and collection are accomplished through a syringe driven probe on an XYZ drive platform controlled by sophisticated software to move the probe in three translation directions (i.e. along the X, Y, Z axes). The sampling probe is mounted on a rotatable head that allows the probe to be tilted between a vertical orientation and an angled orientation. The precise angle may be fixed using a stop to match the angle of the sampling arm of the cell. In some embodiments, the rotation of the head may be continuous using an actuator, motor, gears, sprockets, bearings and the like to stop at any angular orientation. The automated system mimics the way sampling, collection, and media replacement are performed by laboratory analysts when working manually, while simultaneously reducing the potential for variances due to procedural inconsistencies. The modular design of the dry-heat block allows laboratories to move smoothly between manual and automated methods when scaling to higher numbers of experiments. The XYZ drive platform works in conjunction with a peg fixed to the housing of the automated system to automatically tilt the sampling probe to an angled orientation for extraction from an angled sampling arm of cell, and to a vertical orientation to deposit extracted samples into collection vials.

The enclosed description of presently preferred embodiments of the invention has been presented for the purposes of illustration and description only. It is not intended to be exhaustive or to limit the invention to the precise form(s) disclosed. Many modifications and variations are possible in light of the above teachings while remaining consistent with the spirit of the invention. It is intended that the scope of the invention not be limited by this detailed description.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The invention of the present application is a diffusion system typically found in the laboratory setting, such as for scientific, biological, pharmaceutical, biotechnological studies, and the like, where the mixing of a solute into a solvent is desired to test for various properties of an unknown factor. In the pharmaceutical industry, the rate of diffusion of a pharmaceutical application, for example, through the skin, is important. A diffusion system can mimic such an environment to help optimize a pharmaceutical formulation that produces consistent diffusion rates. In order for a diffusion system to be useful in optimizing a formulation, however, the diffusion system itself must not contribute to variability in results by being capable of thoroughly mixing the test formulation in a solvent, and providing a diffusion system with minimal variations in the construction of the components. In addition, from a manufacturing standpoint, in order to maximize efficiency, the heating of the solution and testing of the samples should be consistent and automatable.

Figure 1A:
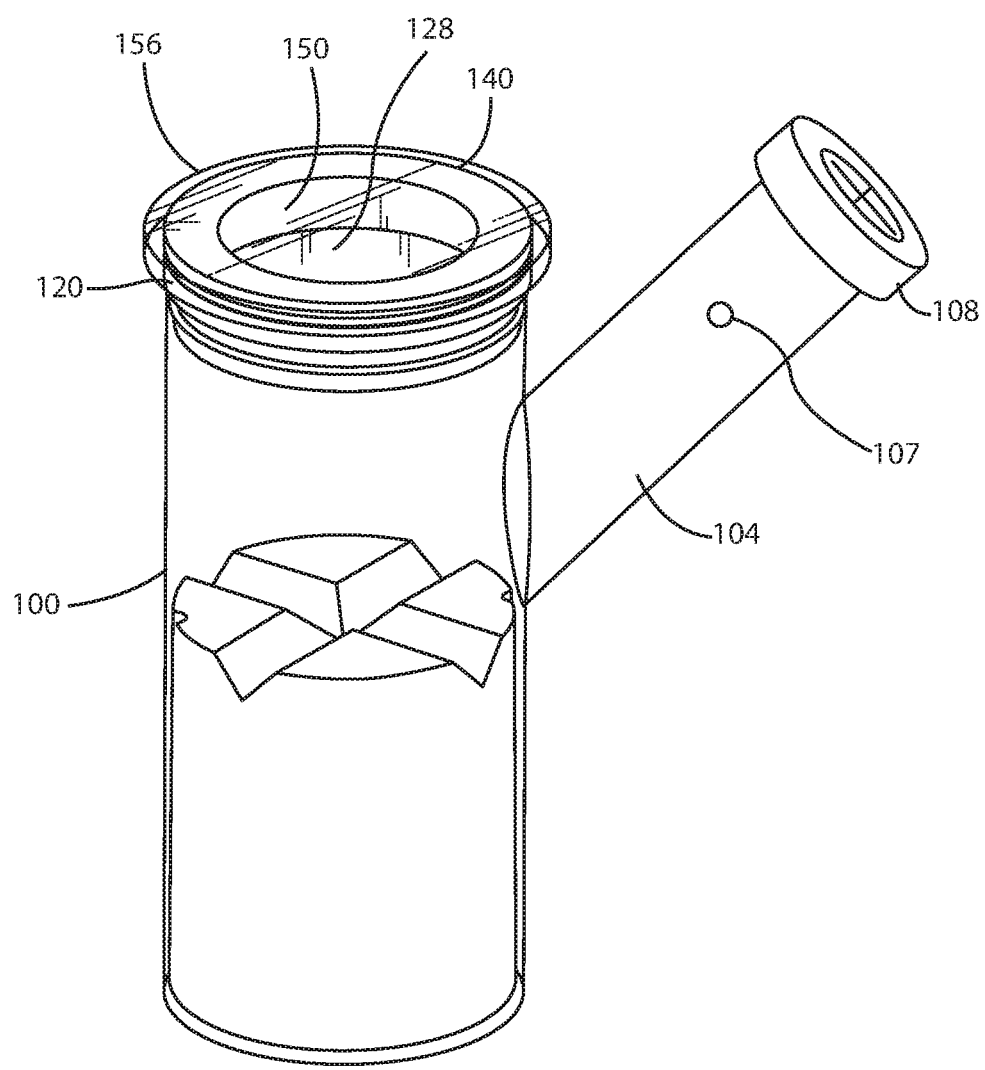
FIG. 1A is a perspective view of an embodiment of the present invention.
Figure 1B:
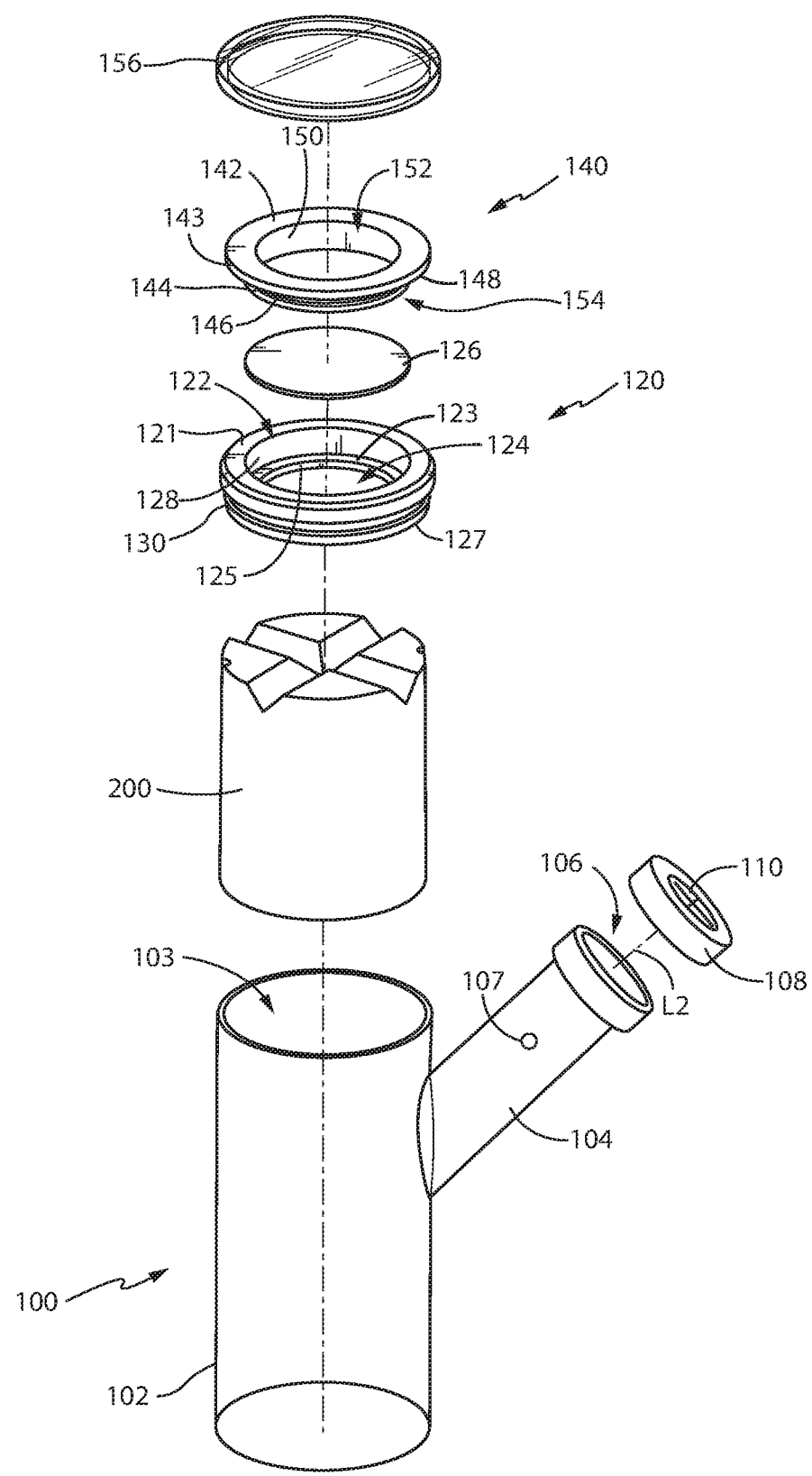
FIG. 1B is an exploded view of the embodiment shown in FIG. 1.
Figure 1C:
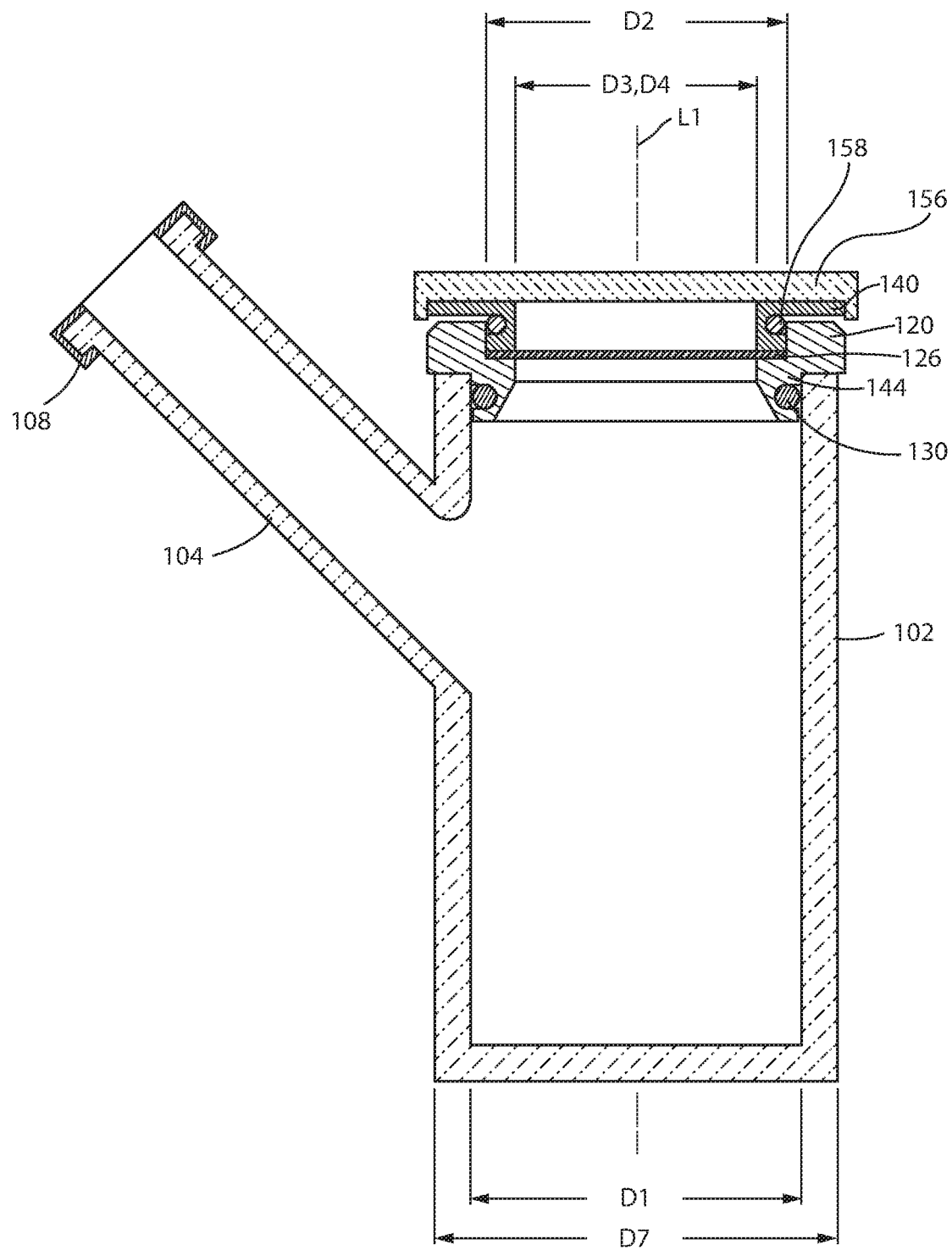
FIG. 1C is a cross-sectional view of the embodiment shown in FIG. 1, cut along line A-A as shown in FIG. 4, with the mixer removed.
Figure 1D:
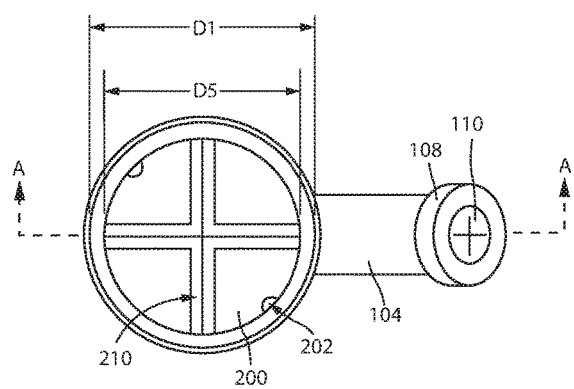
FIG. 1D is a top view of the embodiment shown in FIG. 1 with the cell cap, dosage lid, and dosage lid cover removed.
Figure 1E:
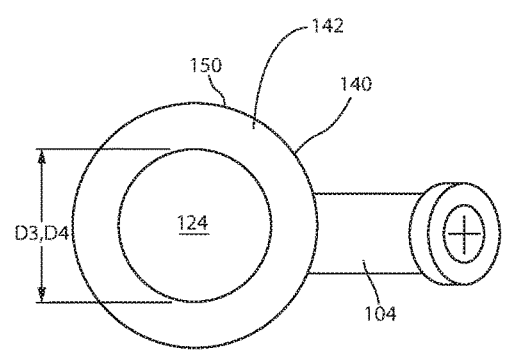
FIG. 1E is a top view of the embodiment shown in FIG. 1 with the mixer removed.
Figure 2A:
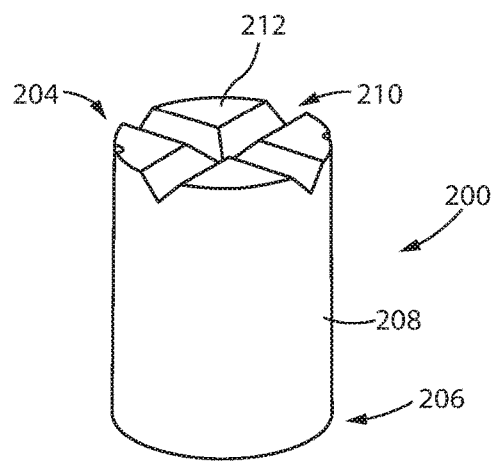
FIGS. 2A-2C show a top perspective view, an elevation view, and a bottom perspective view, respectively, of the mixer.
Figure 2B:
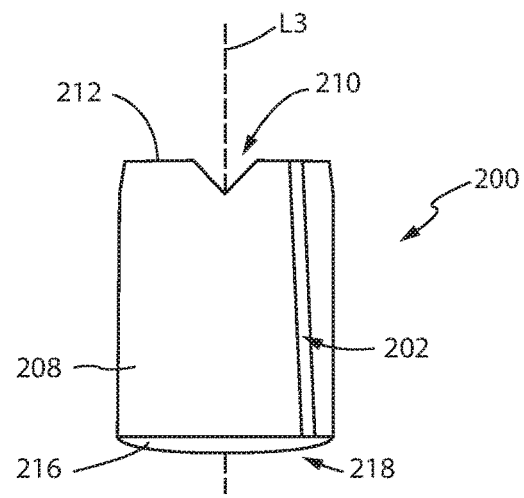
Figure 2C:
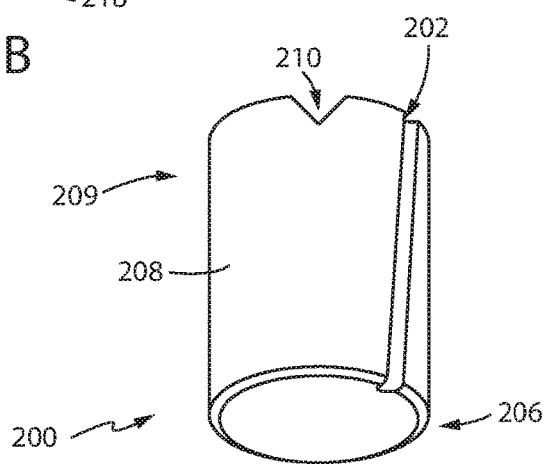
Figure 3A:
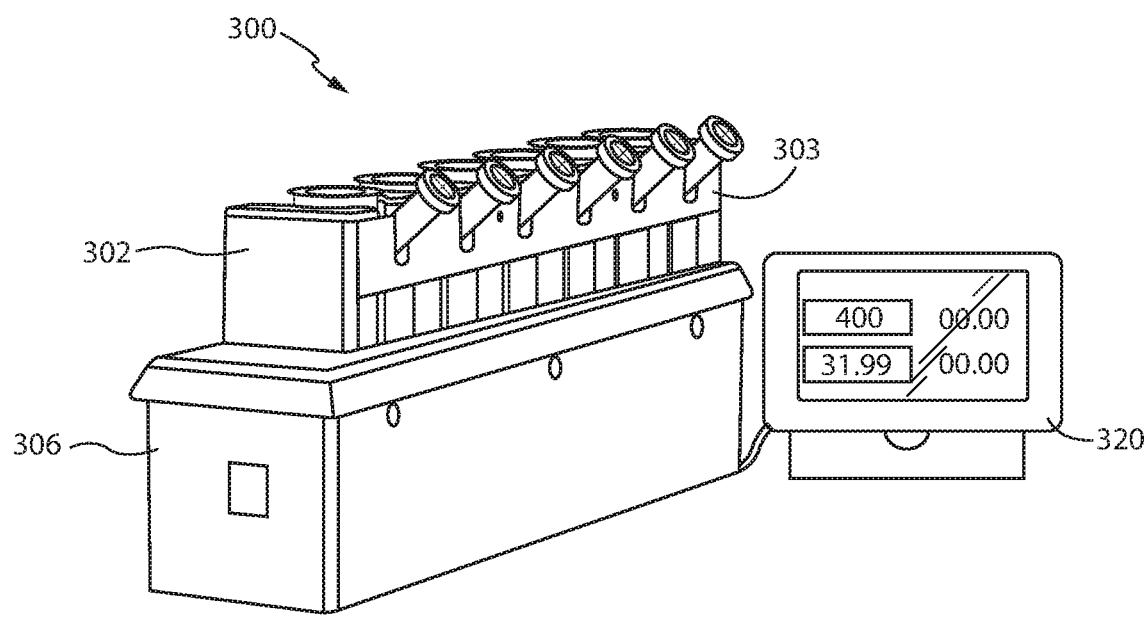
FIG. 3A shows a perspective view of an embodiment of the heating and stirring system.
Figure 3B:
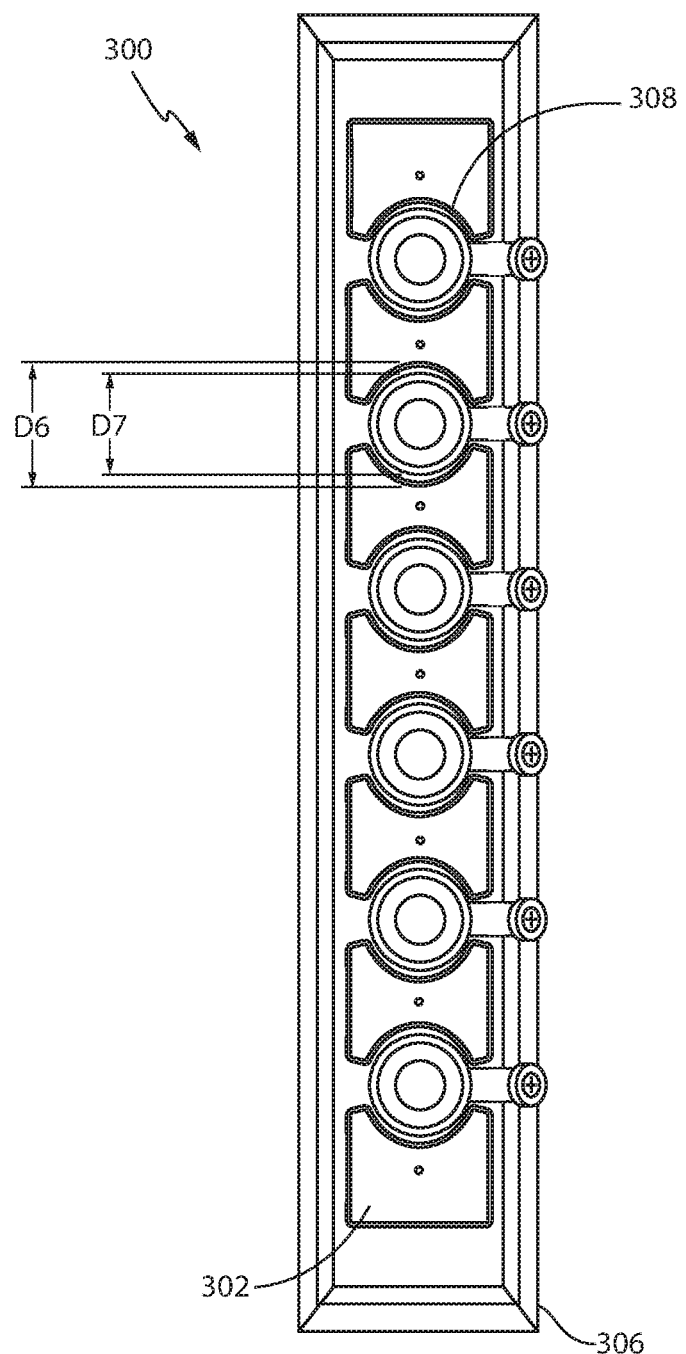
FIG. 3B shows a top view of the heating and stirring system shown in FIG. 3A.
Figure 3C:
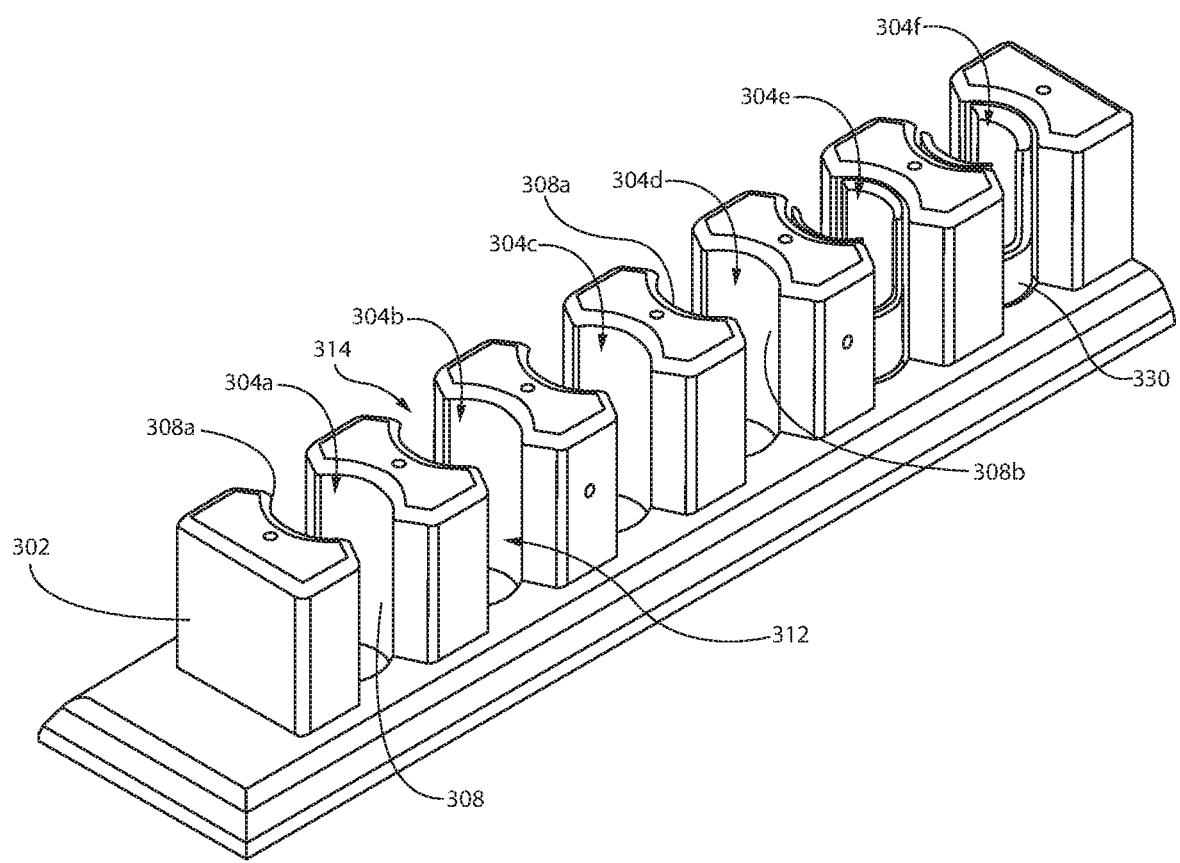
FIG. 3C shows a perspective view of an embodiment of the dry heat block shown in FIG. 3A.
Figure 3D:
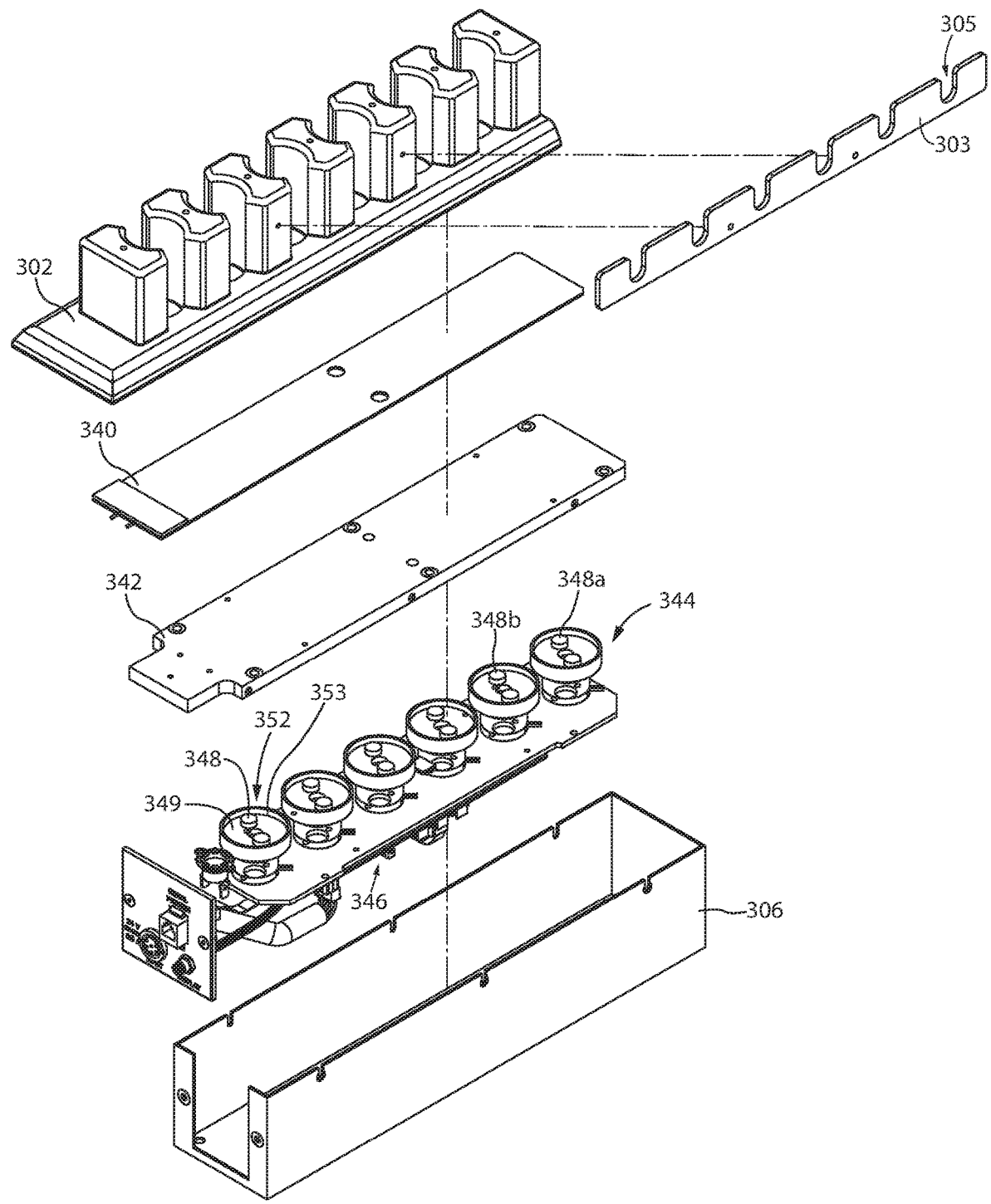
FIG. 3D shows an exploded view of the heating and stirring system shown in FIG. 3A.
Figure 3E:
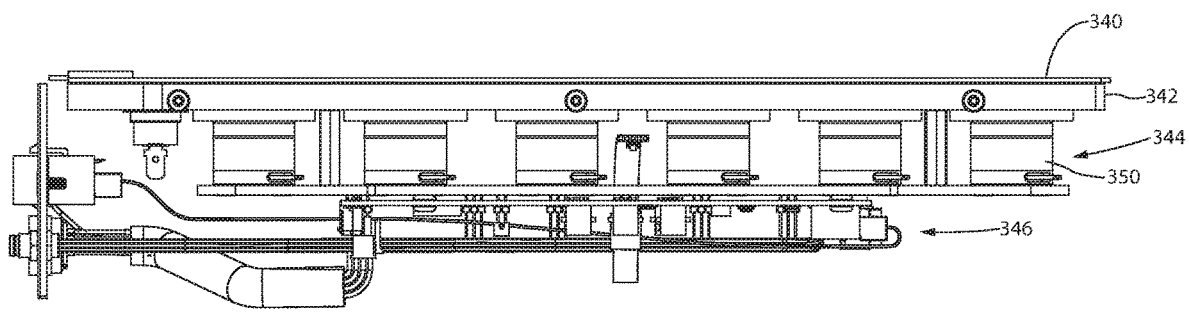
FIG. 3E shows a side elevation view of the heating and stirring system without its housing or the dry heat block to show the internal components.

The diffusion system comprises a uniquely configured container, referred to as a cell 100 (as shown in FIGS. 1A-1E), for containing a receptor medium and for allowing samples of the receptor medium to be taken quickly, easily, and efficiently. In some embodiments, the diffusion system comprises a mixer 200 (as shown in FIGS. 2A-2C) to effectively mix the receptor medium in the cell 100. In some embodiments, the diffusion system comprises the cell 100 and the mixer 200. The mixer 200 is configured to fit inside the cell 100 to mix the receptor medium in the cell 100. In some embodiments, the diffusion system comprises the cell 100, the mixer 200, and a heating system 300 to heat the receptor medium as shown in FIGS. 3A-4B. The heating system 300 also has the capability of causing the mixer 200 to rotate within the cell 100. When a compound is added to the receptor medium, the mixer 200 thoroughly mixes the compound into the receptor medium. In some embodiments, to automate the process, the diffusion system may further comprise an automated sampling and collection station 400. The mixer 200 can be placed in the cell 100, the cell 100 placed in the heating system 300, and the heating system 300, placed in the automated sampling and collection station 400 as shown in FIG. 5A. The automated sampling and collection station 400 can be programmed to automatically collect a sample from the cell 100 for analysis.

With reference to FIGS. 1A-1E, the cell 100 is designed for precision, versatility, and ease-of-use in diffusion-testing labs. The cell 100 comprises a main body 102 having an open top 103, and a sampling arm 104 having an opening 106 branching from the main body 102. Preferably, the main body 102 is cylindrical in shape defining a longitudinal axis L1 and an inner diameter D1. The sampling arm 104 may also be cylindrical defining an longitudinal axis L2. In the preferred embodiment, the sampling arm 104 is angled upwardly such that the longitudinal axis L2 of the cell 100 and the longitudinal axis L2 of the sampling arm 104 form an acute angle when measured from the top side.

The opening 106 in the arm 104 is preferably large enough to accommodate standard pipette tips. The opening 106 in the arm 104 may be covered with a cover 108. The cover 108 may have one or more flaps 110 to cover the opening 106. The flaps 110 are movable so that a pipette can be inserted into the opening 106 through the cover 108 without having to remove the cover 108. Insertion of a pipette tip through the cover causes the flaps 110 to bend inwardly into the arm 104. Removal of the pipette tip from the cover causes the flaps to return to their original configuration of closing the opening 106. A convenient fill mark 107 may be placed on the sampling arm 104 to indicate to the user how much to fill the cell 100.

For maximum versatility, users can choose from small, medium, or large borosilicate glass cells. The effective volume of the receptor medium in the cell 100 can be varied by using different sized mixers 200. By way of example only, mixers 200 of various sizes can be used to vary the volume of the receptor medium from about 10 mL to about 30 mL, all in the same cell 100 or in 3 different size cells.

In the preferred embodiment, the diffusion system is designed to measure the rate of diffusion of a compound through a semi-permeable barrier, such as, but not limited to, skin. As such, the cell 100 may further comprise a cell cap 120 that can be placed on top of the cell 100 at the open top 103. The cell cap 120 comprises a sidewall 127 projecting downwardly. The sidewall 127 comprises an outer perimeter and an inner wall 128 defining a cap orifice 122 to allow access into the cell 100 through the open top 103, the inner wall 128 of the cell 100 having a diameter D2. Specifically, the cell cap 120 has a top surface 121 defining the cap orifice 122, the cap orifice 122, through which a compound being tested has access to the cell 100, and a recessed floor 123 defining an output orifice 124, the output orifice having a diameter D3 through which the compound exits the cell cap 120 and enters into the cell 100. A membrane 126 may be attached to the floor 123 to cover the output orifice 124. The membrane 126 mimics the semi-permeable barrier through which the rate of diffusion is being tested. To assure a watertight seal between the cell 100 and the cell cap 120, a seal 130, such as an o-ring seal, may be mounted on the outer perimeter of the sidewall 127 of the cell cap 120 in between the sidewall 127 and the cell 100.

Due to the floor 123 being recessed relative to the top surface 121, the cell cap 120 defines the inner wall 128. The inner wall 128 and the floor 123 define the cap orifice 122 to receive the compound to be tested and provide access to the cell 100. Sufficient amount of receptor medium is added to the cell 100 such that when the cell cap 120 is properly mounted on the cell 100, the membrane 126 makes contact with the receptor medium so that the compound in the cap orifice 122 can diffuse through the membrane 126 into the cell 100 via the output orifice 124.

In some embodiments, the diffusion system may comprise an array of cell cap kits that accommodates, but is not limited to, 25 mm membranes. As such, in the preferred embodiment, the cap orifice 122 may have a diameter D2 of approximately 25 mm. The output orifice 124 may have diameters D3 ranging from approximately 9 mm to approximately 20 mm, and can accommodate dosage volumes from 0.25 mL to 6.2 mL. The height of the interior sidewall 128 of the cell cap 120 can range from approximately 0.5 mm to approximately 2.6 mm. To accommodate larger volumes or thicker membranes, the height of the interior sidewalls 128 can measure up to 3 mm, 4 mm, 5 mm, or more. The cap orifice diameter D2 and the output orifice diameter D3 can also be increased or decreased; however, the dimensions are designed to work with commonly available membrane sizes, such as the 25 mm filters, although other sizes may be used.

In some embodiments, the membrane 126 may be secured to the cell cap 120 using a dosage lid 140. The dosage lid 140 is configured to fit on top of the cell cap 120 with the membrane 126 residing therebetween. The dosage lid 140 comprises a rim 142 having an outer perimeter 143, and a sidewall 144 projecting downwardly from the rim 142. The sidewall 144 has an outer wall 146 that is recessed radially inwardly relative to the outer perimeter 143 of the rim 142; thereby defining a lip 148 on the underside of the rim 142. The dosage lid 140 further comprises an inner wall 150 defining a lid orifice 152 extending from the rim 142 to the bottom end 154 of the sidewall 144. The lid orifice 152 has a diameter D4 that is substantially similar to the diameter D3 of the output orifice 124 of the cell cap 120. When the dosage lid 140 is placed on top of the cell cap 120, the sidewall 144 enters the cap orifice 122. With a membrane 126 positioned inside the cell cap 120, the bottom of the sidewall 144 of the dosage lid 140 rests on the top side of the membrane 126, and the bottom side of the membrane 126 rests on the floor 123 of the cell cap 120. The rim 142 of the dosage lid may rest on the top surface 121 of the cell cap 120 depending on the presence and thickness of the membrane. Therefore, the inner wall 150 of the dosage lid 140 defining the lid orifice 152 aligns substantially with the inner wall 125 of the floor 123 of the cell cap 120. Thus, when the dosage lid 140 is installed, the effective volume available to hold the test compound is based on the diameter D4 of the lid orifice 152 and the height of the inner wall 150 of the dosage lid 140. O-rings 130, 158 facilitate in ensuring sealing and precise alignment of the orifices.

The cell cap 120 and dosage lid 140 are machined to very tight tolerances so that the output orifice 124 of the cell cap 120 aligns precisely with the lid orifice 152 of the dosage lid 140 to ensure uniform and consistent surface area exposure of the exposed membrane 126 from one cell 100 to the next, thereby leading to reduced variability. The exposed membrane 126 is the portion of the membrane 126 that is exposed to the compound being tested when the dosage lid 140 is properly mounted on the cell cap 120. Essentially, the exposed membrane 126 is the portion of the membrane exposed through the lid orifice 152 of the dosage lid 140. This configuration allows for consistent measurements of compound diffusion through the membrane 126 into the receptor medium where the compound is mixed. Although a watertight fit may be created between the outer wall 146 of the dosage lid 140 and the inner wall 128 of the cell cap 120, to further assure a watertight fit between the dosage lid 140 and the cell cap 120, a seal 158, such as an o-ring seal, may be mounted on sidewall 144 of the dosage lid 140.

Traditionally, solutions are mixed in the laboratory setting using a stir bar. The stir bar is essentially a small rod-shaped magnetic bar. When placed on top of a magnetic stirrer, the stir bar rotates to stir the solution. In general, the stir bar is selected to have a length that is close to the diameter of the beaker in which the solution is being stirred. Because the stir bar is rod-shaped, it does not occupy much surface area or volume in the beaker.

The diffusion system of the present application utilizes a uniquely configured mixer 200 to replace the traditional stir bars. As shown in FIGS. 2A-2C, in the preferred embodiment, rather than being rod-shaped, the mixer 200 of the present invention is cylindrical in shape defining a longitudinal axis L3 and a diameter D5. The inner diameter D1 of the cell 100 is substantially the same as the diameter D5 of the mixer 200, such that the mixer 200 fits inside the cell 100 and has sufficient space to rotate inside the cell 100, but occupies a large portion of the surface area of the cell 100.

By way of example only, the mixer 200 may occupy approximately 75 percent to approximately 99 percent of the surface area of the cell 100. Preferably, the mixer 200 occupies approximately 80 percent to approximately 99 percent of the surface area of the cell 100. More preferably, the mixer 200 occupies approximately 90 percent to approximately 99 percent of the surface are of the cell 100.

The mixer 200 comprises a top 204, a bottom 206 opposite the top 204, and a sidewall 208 therebetween. As with typical stir bars, the mixer 200 has a magnet operatively connected to it. The magnet may be hidden inside the mixer 200, placed on the outer surface, located at the bottom, or any other location in or on the mixer 200 that allows the mixer 200 to spin when placed on a stirring plate.

In the preferred embodiment, the mixer 200 comprises a longitudinal groove 202. The longitudinal groove 202 may be formed into the sidewall 208, and extends from the top 204 of the mixer 200 to the bottom 206 of the mixer 200.

More preferably, the longitudinal groove 202 is angled relative to the longitudinal axis L3 of the mixer 200. In some embodiments, the longitudinal groove 202 may be curved. As such, the longitudinal groove 202 may follow a slightly spiraled path. The configuration of the longitudinal groove 202 allows the mixer 200 to pump the receptor medium throughout the cell 100; thereby enhancing the mixing effect of the mixer 200.

In some embodiments, to enhance the mixing effect of the mixer 200, the mixer may further comprise an irregularity 210 at the top 204. In other words, the top surface 212 of the mixer 200 is not completely flat. Rather, the top surface 212 may comprise such irregularities 210 as undulations, projections, crevices, fins, peaks and valleys, bumps, dimples, and the like. In the preferred embodiment, the irregularity 210 is a transverse groove formed in the top surface 212 of the mixer 200. In the preferred embodiment, the irregularity may be two transverse grooves intersecting approximately in the middle of the mixer 200.

In some embodiments, to enhance the mixing effect, the bottom surface 216 of the mixer 200 is configured to improve the spinning of the mixer 200. For example, the bottom surface 216 may comprise a downward projection 218. Once the mixer 200 begins spinning, the momentum of the spin allows the mixer 200 to balance and spin on the downward projection 218. The downward projection 218 reduces the surface area upon which the mixer spins; thereby, reducing the drag or resistance along the bottom surface of the cell 100. The downward projection 218 may be a short rod extending out from the middle of the bottom surface 216 of the mixer 200, concentric with the longitudinal axis L3 of the mixer 200. The downward projection may be created by a curvature along the bottom surface 216 of the mixer 200. In other words, the bottom of the mixer 200 may be convex.

To mimic diffusion in a biological system, as shown in FIGS. 3A-3E, the diffusion system may further comprise a heating and stirring system 300 to heat the receptor medium in the cell 100. The heating and stirring system 300 comprises a dry heat block 302, the dry heat block 302 comprising a plurality of bays 304a-f to receive a plurality of cells 100. The dry heat block 302 can be mounted on a heating and stirring plate housing 306, which comprises a heating element 340 and a stirring mechanism 344 to heat each bay 304a-f and stir each mixer 200 within any of the bays 304a-f.

Each bay 304a-f of the dry heat block 302 is defined by a cylindrical wall 308 having an inner diameter D6. The inner diameter D6 of the bay 304a-f is substantially similar to the outer diameter D7 of the cell 100 so that the bay 304a-f can receive the cell 100, but remain sufficiently close to effectively transfer heat from the cylindrical wall 308 to the cell 100. Preferably, each cylindrical wall 308 defines a slot 312 to accommodate the arm 104 of the cell 100 when the cell 100 is inserted into one of the bays 304a-f. The slot 312 may be formed by a cutout into the cylindrical wall 308. The cutout may be sufficiently deep so as to clear the arm 104 of the cell 100 when placed in a bay 304a-f. In some embodiments, the slot 312 may extend the full height of the cylindrical wall 308, effectively splitting the cylindrical wall 308 into two partial walls 308a, 308b. In such an embodiment, a restraint plate 303 may be attached to the sides of the cylindrical walls 308 to effectively prevent the cells 100 from rotating within their respective bays 304a-f. Preferably, a single restraint plate 303 can span across each of the slots 312 on one side of the cylindrical wall 308. The restraint plate 303 may have a series of cutouts 305 to accommodate the arm 104 of the cell 100. The cutouts 305 effectively catch the arm 104; thereby restraining rotational movement of the cell 100. In some embodiments, the cylindrical wall 308 may comprise two slots 312, 314. Preferably, the two slots 312, 314 are bilaterally arranged to be on diametrically opposing sides. While one slot 312 can be used to accommodate the arm 104 of the cell 100, the second slot 314 can be used to inspect the contents of the cell 100 after it has been placed in the dry heat block 302. For example, if the user desires to inspect the cell 100 for receptor medium levels, bubbles, rotation of the mixer, and the like, the user can look through the second slot 314 either directly or with the assistance of a mirror.

The cylindrical walls 308 of the dry heat block 302 are configured to surround the cell 100 so as to be able to heat the contents of the cell 100. As such, each cylindrical wall 308 may contain heating elements to directly heat the cells 100 or transfers heat form the heat plate 340 effectively. Therefore, a water bath is not necessary. Due to the cylindrical wall 308 configuration, heating of the cell 100 is just as effective as a water bath, but with better control.

In the preferred embodiment, in order to provide uniform heat distribution across each bay 340a-f, heat is generated by a heating element 340, such as a heater pad, underneath the heat block 302. The heating element 340 may be a single pad that extends from a bay 304a at one end to the bay 304f at the opposite end. Heat generated from the heating element 340 is transferred to the heat block 302 and then to the cells 100. In some embodiments, each bay 304a-f may have its own heating element 340. The heating element 340 is operatively connected to a controller 320 that can control the temperature of the dry heat block 302. In some embodiments, the temperature of each bay 304a-f may be controlled separately. In some embodiments, all of the bays 304a-f are operatively connected together and are controlled together.

Below the heating element 340 is a heat block plate 342. The heat block plate 342 may be a solid aluminum plate that provides a flat surface upon which the heating element 340 rests. The heat block plate 342 may evenly press the heating element 340 against the bottom of the heat block 302 for even heat distribution to the heat block 302.

The controller 320 may be operatively connected to the dry heat block 302 either through a wireless connection or a wired connection. Preferably, the controller 320 runs on an embedded single-board computer to control the heat generated by the heating system 300 and the rotational speed of the stirring mechanism 344. Preferably, the controller 320 comprises an interactive touch screen. The controller 320 may be programmable to activate the dry heat block 302 and the stirring mechanism 344. The user can set parameters such as the temperature of the dry heat block 302, the speed of rotation for the stirring mechanism 344, the time for the heating element 340 and the stirring mechanism 344 to be on, and the like.

Below the heat block plate 342 is the stirring mechanism 344. The stirring mechanism 344 comprises components that are typical of traditional stir plates. For example, in the preferred embodiment, the mixer 200 comprises a magnet; therefore, the stirring mechanism 344 also utilizes a stirrer 348, preferably in the form of a rotating magnet or magnets to cause the mixer 200 to rotate. The stirrer 348 may comprise a rotatable disc 349 that is operatively connected to a motor 350 to control the speed of rotation. In the preferred embodiment, each bay 304a-f has its own stirrer 348 and motor 350. As such, each bay 304a-f can regulate its stirring speed independent of the other bays 304a-f. Circuitry 346 underneath the stirring mechanism 344 can be used to control the speed of rotation of each stirrer 348 independent of one another. As such, the circuitry 346 may also be operatively connected to the controller 320.

As each stirrer 348 is aligned in series adjacent to each other, there can be interference between the magnets. As such, in some embodiments, each stirrer 348 may be housed in its own cup 352 with a wall 353 that rise above the stirrer 348 to shield one stirrer 348a from a neighboring stirrer 348b. In some embodiments, the heat block plate 342 may further comprise a series of recesses along the bottom of the heat block plate 342 that correspond with the cups 352. The recesses may be sized and dimensioned to receive at least a top portion of the cups 352. Such an arrangement may provide additional shielding against neighboring stirrers 348a, b interfering with each other.

Figure 4A:
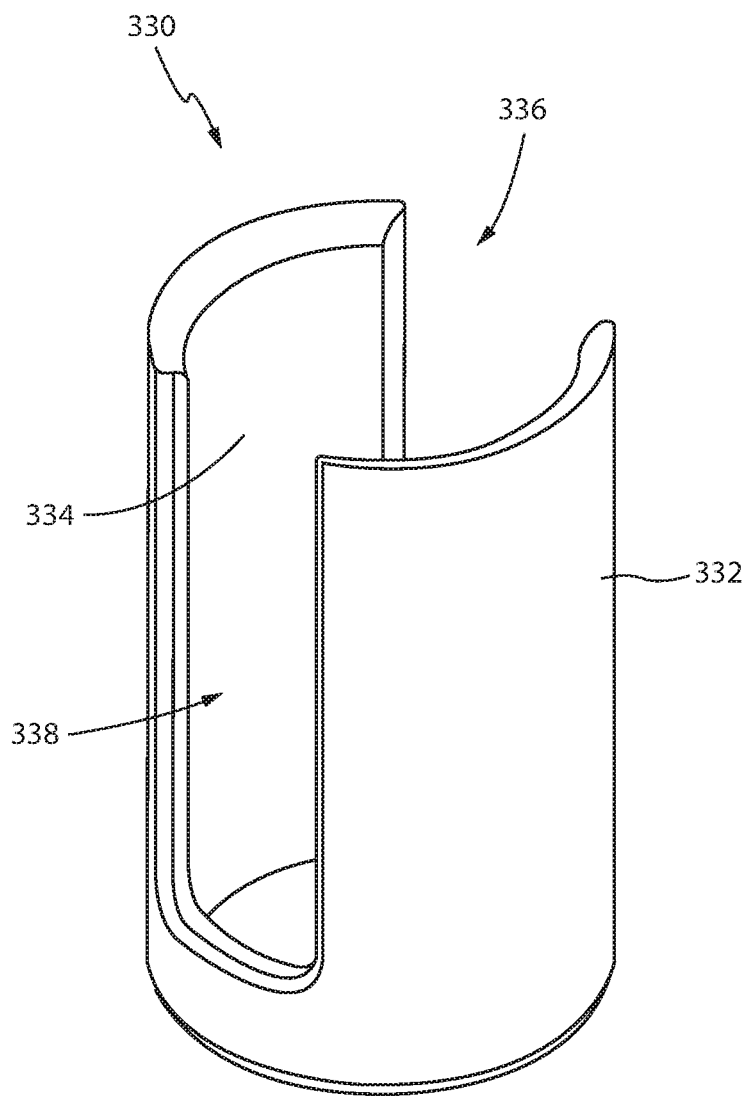
FIGS. 4A-4B show a perspective view and an elevation view, respectively, of an embodiment of a sleeve.
Figure 4B:
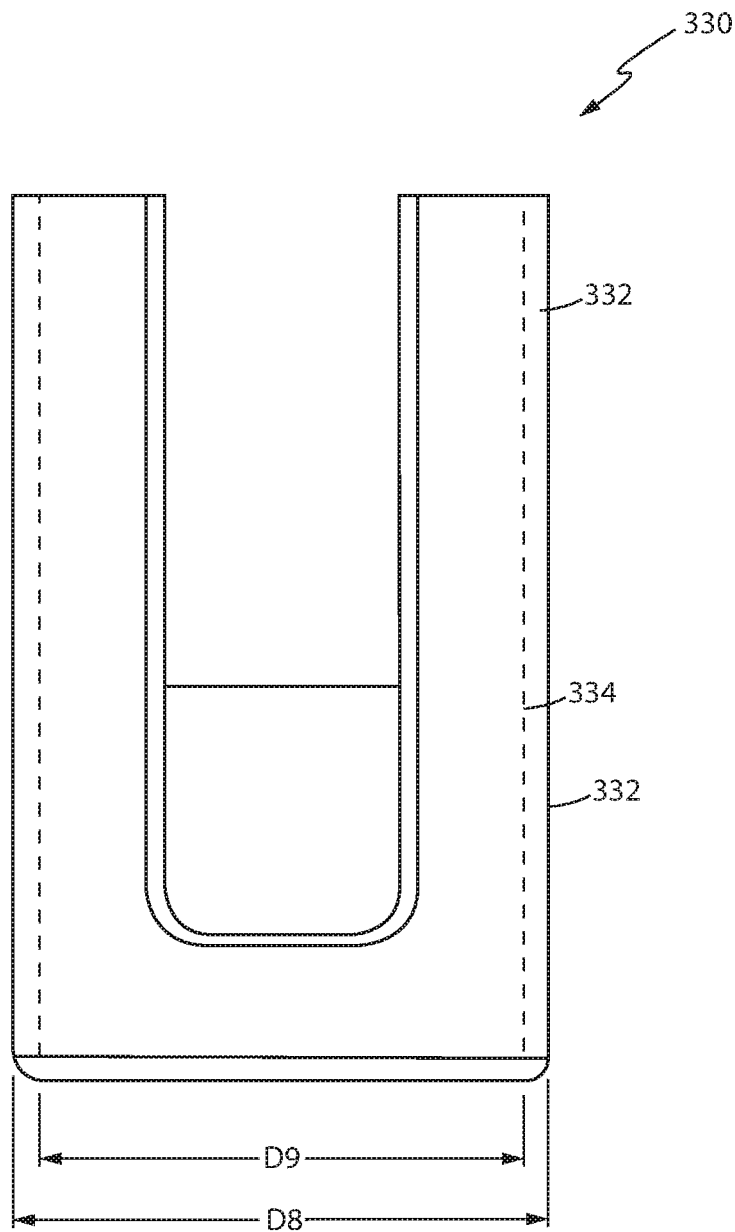
Figure 5A:
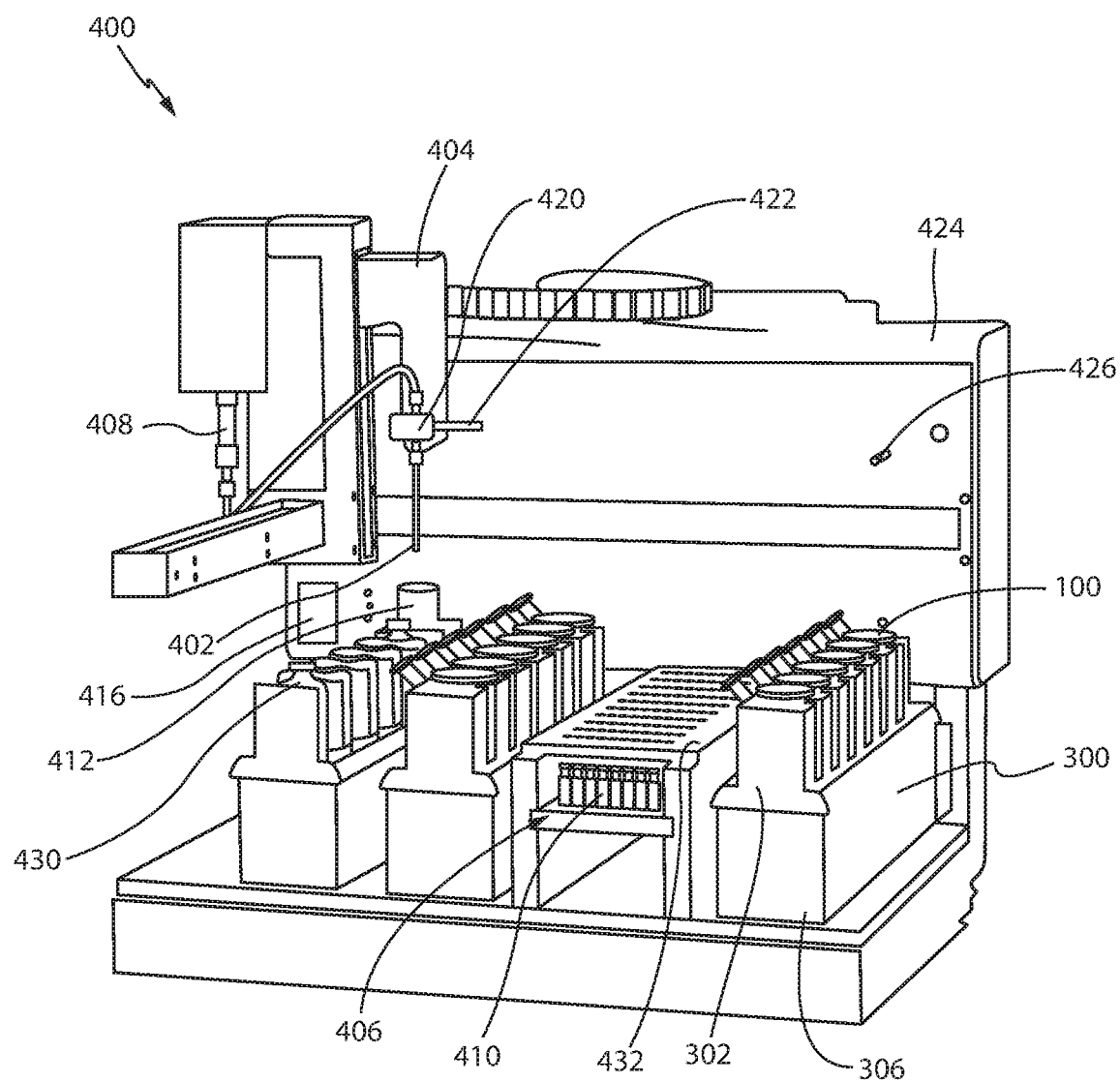
FIG. 5A shows an embodiment of the automated sampling and collection station.

With reference to FIGS. 4A and 4B, in order to accommodate cells 100 of different sizes in the same dry heat block 302, the heating system 300 may further comprise a sleeve 330 insertable into any one of the plurality of bays 304a-f, such that heat generated in the bay 304a-f into which the sleeve 330 has been inserted, is transferred to the sleeve 330. The inner diameter D6 of each bay 304a-f is substantially the same size as the outer diameter D7 of the largest cell 100 anticipated to be used. To accommodate smaller cells 100, the sleeve 330 is used. The sleeve 330 comprises an outer wall 332 having an outer diameter D8 that is substantially equivalent to the inner diameter D6 of the cylindrical wall 308 defining the bay 304a-f. The sleeve 330 comprises an inner wall 334 defining an inner diameter D9 that is substantially equivalent to the outer diameter D7 of the cell 100 to be received by the sleeve 330. Therefore, only the inner diameter D9 of the sleeve 330 changes across sleeves 330 of different sizes to accommodate cells 100 of different sizes, while the outer diameters D8 of the various sleeves 330 remain the same to fit into the bays 304a-f of the dry heat block 302.

To accommodate the arm 104 of the cell 100, the sleeve 330 may also comprise a slot 336. Like the bay 304a-f, the sleeve may comprise a second slot 338 through which the contents of the cell 100 can be examined.

With reference to FIG. 5A, in some embodiments, the sampling, collection, and testing of the test compound can be automated using an automated sampling and collection station 400. Thus, once the user has prepared all the samples in the cell 100, the cell 100 can be placed in the heating system 300, and the heating system 300 placed in the automated sampling and collection station 400. The controller 320 can be operatively connected to the automated sampling and collection station 400 and programmed to execute the processes described herein. In the embodiment with the automated sampling and collection station 400, the controller 320 may be a computer or incorporated into a computer, and specially programmed to execute the steps described herein.

The automated sampling and collection station 400 comprises a syringe driven probe 402 configured to move in three translation directions, namely the XYZ directions of three dimensional space, by being attached to a drive platform 404. The drive platform 404 moves the probe 402 in three dimensional space. A set of samples in the heating system 300 can be placed on the automated sampling and collection station 400 below the probe 402. The drive platform 404 can be programmed to drive the probe 402 in three dimensional space to take sample aliquots from each or any cell 100, and then deposit the sample aliquot into a vial 410 on a collection tray 406. The collection tray 406 may comprise a plurality of vials 410. The drive platform 404 can be programmed to move the probe 402 in a manner that allows the probe to deposit various aliquots into the proper vials 410.

In order to take the sample aliquots from the cell 100, the probe 402 may be operatively coupled to a syringe 408. The syringe 408 can be actuated at the proper time to remove an aliquot from a cell 100.

In general, when in use, the probe 402 is tipped or angled so that the probe 402 is parallel with the arm 104 of the cell 100. The probe 402 is then taken to a cell 100 to extract a sample. The probe 402 is then tipped or returned back to the vertical orientation. The probe 402 is then take to the collection tray 406. When the probe 402 is placed over the collection tray 406, the syringe 408 can be reversed to release the aliquot into one of the vials 410 in the collection tray 406. Once the deposit is complete, before moving to the next sample, the drive platform 404 may move the probe 402 to a wash station 412, where the probe 402 can be washed. The wash station 412 may access a container containing a wash solution. A pump 416 may be operatively connected to the wash station 412 to constantly provide clean wash solution to the wash station from the wash container. In addition, the syringe 408 may be actuated and reversed multiple times while the probe 402 is in the wash solution to wash out the inside of the probe 402. Once the probe 402 has been sufficiently cleansed, the probe may be taken to a media bottle 430 to draw up replacement media with the syringe 408. The probe is then tipped or angled again parallel to the arms 104, returned to the original cell 100 from which the sample was drawn, and deposit the replacement media into the original cell 100 to return the receptor solution back to its original volume prior to taking of the sample.

In the preferred embodiment, the arm 104 of the cell 100 in which the receptor medium is contained projects at an angle relative to the longitudinal axis L1 of the cell 100. As such, in the preferred embodiment, the probe 402 may be mounted on a rotatable head 420 that allows the probe 402 to tilt between a vertical orientation parallel to the longitudinal axis L1 of the cell 100 (when properly placed on the automated sampling and collection station 400), and an angled orientation parallel to a longitudinal axis L2 of the arm 104.

Tilting the probe 402 from a vertical orientation to an angled orientation may be accomplished using a stop. The stop can be positioned on or near the rotatable head 420 to obstruct movement of the rotatable head 420 beyond the desired angle. For example, the stop may be a protrusion, a ball detent, a magnet, and the like. In some embodiments, the rotation of the rotatable head 420 may be continuous using gears, sprockets, bearings, and the like, to stop at any angular orientation. In some embodiments, the rotatable head 420 may be operatively connected to a motor to automatically move the rotatable head 420 to the desired orientation.

Figure 5B:
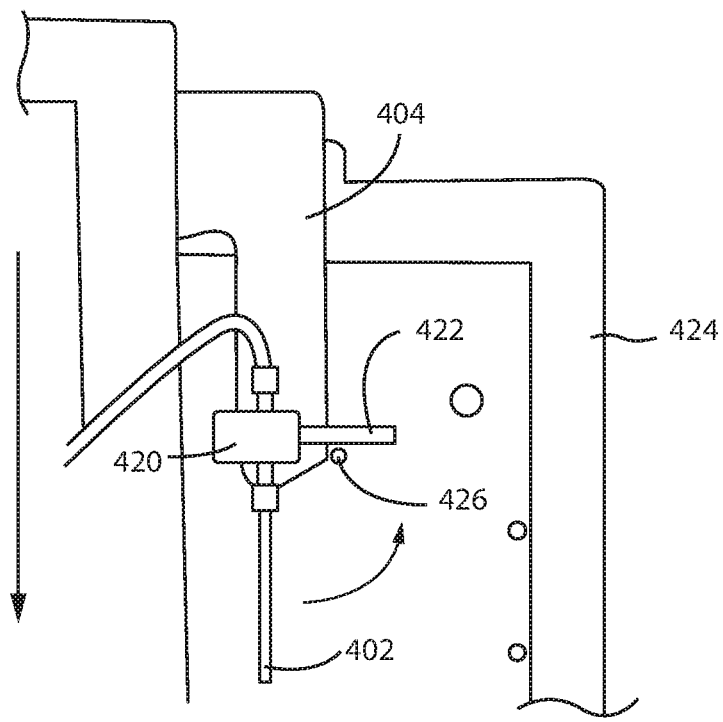
FIGS. 5B-5E demonstrate how the probe can be tilted from a vertical orientation to an angled orientation and back to the vertical orientation.
Figure 5C:
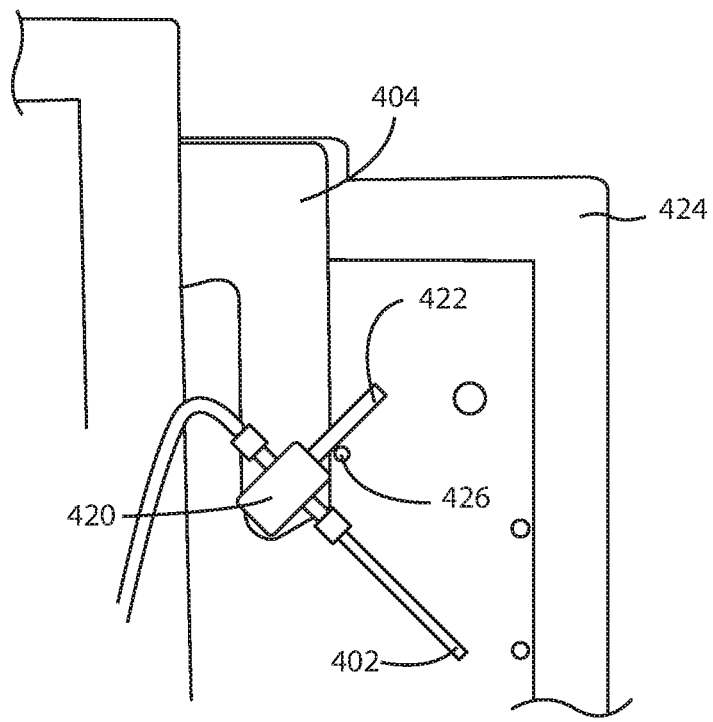

In the preferred embodiment, the rotating head 420 comprises a rod 422, and the housing 424 of the automated sampling and collection station 400 comprises a peg 426 projecting perpendicular to the direction of the rod 422. Coordinated movement of the probe 402 relative to the peg 426 allows the peg 426 to tilt the probe 402 between the vertical orientation and the angled orientation. For example, the drive platform 404 moves the probe 402 towards the peg 426 with the rod 422 above the peg 426 as shown in FIG. 5B. Once the rod 422 is directly over the peg 426, the drive platform 404 moves the rotatable head 420 downwardly causing the rod 422 to abut against the peg 426. Because the rod 422 is unable to move due to the peg 426, the rotatable head 420 rotates in a first rotational direction to allow the rotatable head 420 to continue its downward motion. Rotation of the rotatable head 420 in the first rotational direction causes the probe 402 to tilt towards its angled orientation as shown in FIG. 5C. Once the probe 402 reaches the predetermined angled orientation, the rotation of the rotatable head 420 stops, and the probe 402 is now in a configuration to be inserted into an arm 104 of a cell 100. Rotation of the rotatable head 420 can be stopped either by a stop that interferes with the rotation of the rotatable head 420 or due to the drive platform 404 stopping the downward descent of the rotatable head 420.

Figure 5D:
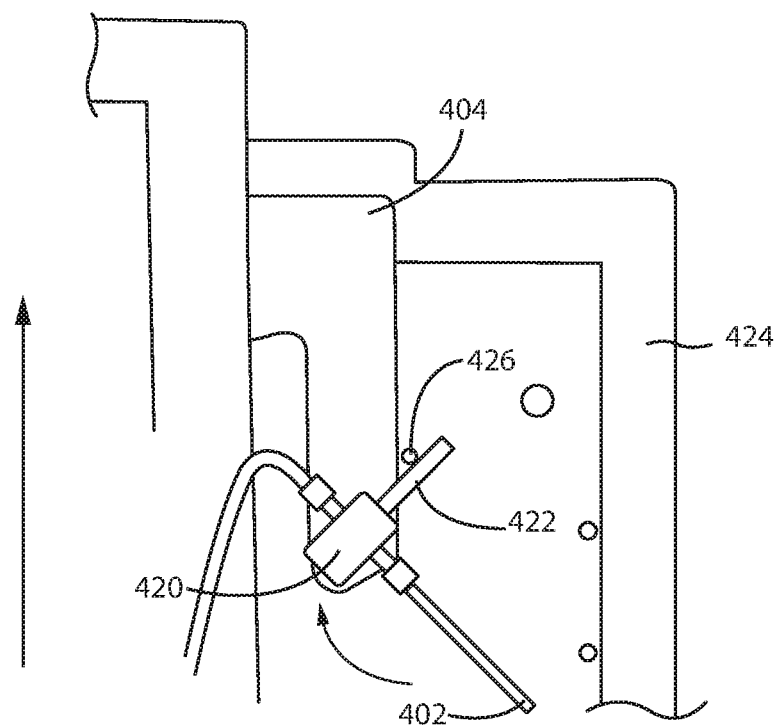
Figure 5E:
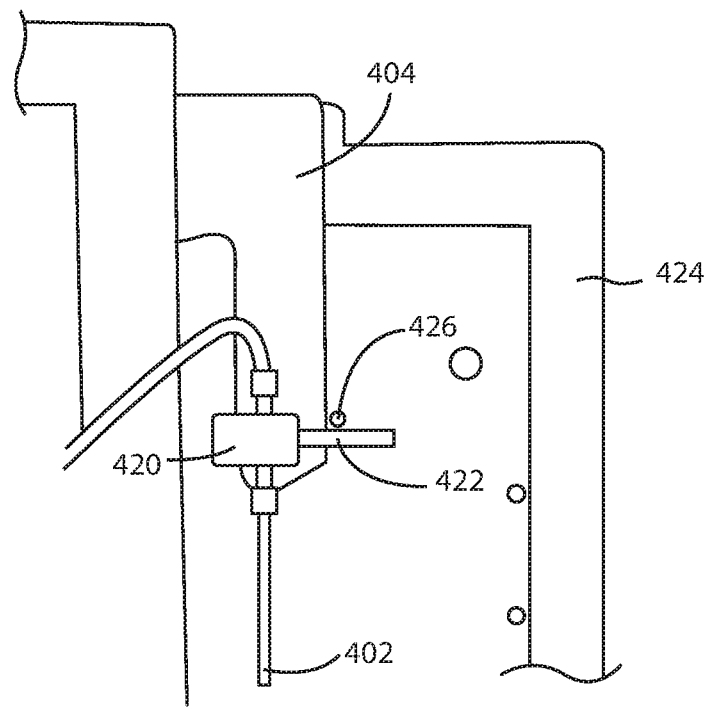

While the probe 402 is in the angled orientation, the drive platform 404 moves the probe 402 to a cell 100 and inserts the probe 402 into the arm 104 of the cell 100. The syringe 408 is then actuated and an aliquot is drawn from the arm 104. The drive platform 404 then withdraws the probe 402 from the arm 104 and moves the rotatable head 420 towards the peg 426, but this time, with the rod 422 below the peg 426 as shown in FIG. 5D. Once the rod 422 is directly below the peg 426, the drive platform 404 raises the rotatable head 420 causing the rod 422 to abut against the peg 426. This causes the rotatable head 420 to rotate in a second rotational direction opposite from the first rotational direction causing the probe 402 to tilt back to its vertical orientation as shown in FIG. 5E. The drive platform 404 moves the probe 402 over one of the vials 410 in the collection tray 406 and deposits the aliquot into the vial by reversing the action of the syringe 408. The drive platform 404 then moves the probe 402 to the wash station 412 to wash the probe 402 in preparation for another extraction.

In some embodiments, a guide plate 432 is positioned on top of the collection tray 406. The guide plate 432 comprises a plurality of holes 434 that align with the vials 410 below. The guide plate 432 helps guide the probe 402 into the vials. In some embodiments, the holes 434 are sized to provide some resistance to the probe 402 without interfering with its movement. The sizing of the holes 434 assures the probe 402 enters the vials 410. In addition, due to the resistance, before the probe 402 is inserted into the vial, any gross debris or contaminants can be removed, and when the probe 402 is retracted out from the vial, any solution on the probe can be wiped off. In some embodiments, the holes 434 may be lined with material to help remove any debris or contaminants from the probe 402 before inserting into the vial, or strip off excess solution from the probe 402 as it is retracted out from the vial 410.

The automated system mimics the way sampling, collection, and media replacement are performed by laboratory analysts when working manually, while simultaneously reducing the potential for variances due to procedural inconsistencies. The modular design of the dry-heat block allows laboratories to move smoothly between manual and automated methods when scaling to higher numbers of experiments. The drive platform works in conjunction with a peg fixed to the housing of the automated system to automatically tilt the sampling probe to an angled orientation for extraction from an angled sampling arm of cell, and to a vertical orientation to deposit extracted samples into collection vials.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

The invention claimed is:

1. A diffusion system, comprising:
   a. a cell for receiving a receptor medium;
   b. a mixer configured to fit inside the cell to mix the receptor medium in the cell;
   c. a cell cap to cover the cell; and
   d. a dosage lid to place on top of the cell cap, wherein the cell comprises a main body having an open top, and a sampling arm branching from the main body, the sampling arm having an opening.

2. The diffusion system of claim 1, wherein the cell cap is configured to fit on top of the cell at the open top, the cell cap comprising a top surface and a floor recessed from the top surface, the floor having an inner wall defining an output orifice having a diameter.

3. The diffusion system of claim 2, wherein the dosage lid is configured to fit on top of the cell cap, the dosage lid comprising an inner wall defining a lid orifice having a diameter, wherein the diameter of the output orifice is equal to the diameter of the lid orifice, such that when the dosage lid is placed on top of the cell cap, the inner wall of the floor of the cell cap and the inner wall of the dosage lid are aligned.

4. The diffusion system of claim 3, further comprising a membrane configured to fit in between the cell cap and the dosage lid.

5. A diffusion system, comprising:
   a. a cell for receiving a receptor medium;
   b. a mixer configured to fit inside the cell to mix the receptor medium in the cell;
   c. a cell cap to cover the cell; and
   d. a dosage lid to place on top of the cell cap, wherein the cell and the mixer are cylindrical, each defining a longitudinal axis, the cell having an inner diameter and the mixer having a diameter, wherein the inner diameter of the cell is substantially the same as the diameter of the mixer, while allowing the mixer to be spin inside the cell.

6. The diffusion system of claim 5, wherein mixer has longitudinal groove.

7. The diffusion system of claim 6, wherein the longitudinal groove is angled relative to the longitudinal axis of the mixer.

8. The diffusion system of claim 7, wherein the mixer comprises a top, a bottom opposite the top, and a sidewall therebetween, wherein the longitudinal groove is formed into the sidewall extending from the top of the mixer to the bottom of the mixer.

9. The diffusion system of claim 5, wherein the mixer comprises a top, a bottom opposite the top, and a sidewall therebetween, wherein the top of the mixer comprises an irregularity.

10. The diffusion system of claim 9, wherein the irregularity is a transverse groove.

11. The diffusion system of claim 5, wherein the mixer comprises a top, a bottom opposite the top, and a sidewall therebetween, wherein the bottom of the mixer comprises a downward projection.

12. A diffusion system, comprising:
   a. a cell for receiving a receptor medium;
   b. a mixer configured to fit inside the cell to mix the receptor medium in the cell;
   c. a cell cap to cover the cell;
   d. a dosage lid to place on top of the cell cap; and
   e. a heating and stirring system, wherein the heating and stirring system comprises a dry heat block, the dry heat block comprising a plurality of bays to receive a plurality of cells, each bay comprising a stirrer configured to rotate the mixer.

13. The diffusion system of claim 12, wherein each bay of the dry heat block is defined by a cylindrical wall having an inner diameter.

14. The diffusion system of claim 13, wherein each bay of the dry heat block defines a slot to accommodate an arm of the cell when the cell is inserted into one of the bays.

15. The diffusion system of claim 14, wherein the heating and stirring system further comprises a sleeve insertable into any one of the plurality of bays, such that heat generated in the bay into which the sleeve has been inserted is transferred to the sleeve.

16. The diffusion system of claim 12, wherein the stirrer comprises a rotatable magnet mounted in a cup.

17. The diffusion system of claim 12, further comprising a controller running on an embedded single-board computer to control the heat generated by the heating and stirring system and to control the stirrer.

18. A diffusion system, comprising:
   a. a cell for receiving a receptor medium;
   b. a mixer configured to fit inside the cell to mix the receptor medium in the cell;
   c. a cell cap to cover the cell;
   d. a dosage lid to place on top of the cell cap; and
   e. an automated sampling and collection station, wherein the automated sampling and collection station comprises a syringe driven probe configured to move in three translational directions.

19. The diffusion system of claim 18, wherein the probe is mounted on a rotatable head that allows the probe to tilt between a vertical orientation and an angled orientation.

20. The diffusion system of claim 19, wherein the automated sampling and collection station comprises a peg, wherein coordinated movement of the probe relative to the peg allows the peg to tilt the probe between the vertical orientation and the angled orientation.

21. The diffusion system of claim 20, wherein the automated sampling and collection station further comprises a collection tray, wherein the probe is configured to:
   a. move to the peg and use the peg to tilt the probe in the angled orientation;
   b. move to the cell and insert into an angled sampling arm of the cell to extract a sample from the receptor medium;
   c. move to the peg and use the peg to tilt the probe in the vertical orientation; and d. move to the collection tray and deposit the extracted sample into a collection vial mounted on the collection tray.

22. The diffusion system of claim 21, wherein the automated sampling and collection station further comprises a wash station, wherein the probe is configured to move to the wash station after depositing the extracted sample into the collection vial and wash the probe in preparation for another extraction.

* * * * *